United States Patent [19]
Hastings

[11] Patent Number: 5,725,568
[45] Date of Patent: Mar. 10, 1998

[54] METHOD AND DEVICE FOR RECANALIZING AND GRAFTING ARTERIES

[75] Inventor: Roger N. Hastings, Maple Grove, Minn.

[73] Assignee: Scimed Life Systems, Inc., Maple Grove, Minn.

[21] Appl. No.: 495,791

[22] Filed: Jun. 27, 1995

[51] Int. Cl.$^6$ ............................................. A61F 2/06
[52] U.S. Cl. ...................... 623/1; 604/93; 606/191
[58] Field of Search ........................... 623/1; 604/93; 606/191-198

[56] References Cited

U.S. PATENT DOCUMENTS

| | | | |
|---|---|---|---|
| 3,808,113 | 4/1974 | Okamura et al. | |
| 4,313,231 | 2/1982 | Koyamada | |
| 4,577,631 | 3/1986 | Kreamer | |
| 4,822,361 | 4/1989 | Okita et al. | 623/12 |
| 4,890,612 | 1/1990 | Kensey | 623/1 X |
| 4,994,033 | 2/1991 | Shockey et al. | 604/101 |
| 5,049,132 | 9/1991 | Shaffer et al. | 604/101 |
| 5,059,178 | 10/1991 | Ya | 604/101 |
| 5,078,726 | 1/1992 | Kreamer | 623/1 X |
| 5,100,429 | 3/1992 | Sinofsky et al. | 606/195 |
| 5,112,305 | 5/1992 | Barath et al. | 604/96 |
| 5,129,883 | 7/1992 | Black | 604/101 |
| 5,201,764 | 4/1993 | Kelman et al. | 623/1 X |
| 5,213,576 | 5/1993 | Abiuso et al. | 604/96 |
| 5,213,577 | 5/1993 | Kratzer | 604/101 |
| 5,213,580 | 5/1993 | Slepian et al. | 623/1 |
| 5,232,444 | 8/1993 | Just et al. | 604/96 |
| 5,254,089 | 10/1993 | Wang | 604/96 |
| 5,256,141 | 10/1993 | Grencheff et al. | 604/101 X |
| 5,261,875 | 11/1993 | Spears | 604/101 X |
| 5,279,546 | 1/1994 | Mische et al. | 604/101 X |
| 5,286,254 | 2/1994 | Shapland et al. | 604/96 X |
| 5,314,409 | 5/1994 | Sarosiek et al. | 604/101 |
| 5,318,531 | 6/1994 | Leone | 604/96 |
| 5,320,604 | 6/1994 | Walker et al. | |
| 5,328,470 | 7/1994 | Nabel et al. | 604/101 |
| 5,328,471 | 7/1994 | Slepian | 604/101 |
| 5,336,178 | 8/1994 | Kaplan et al. | 604/96 X |
| 5,443,495 | 8/1995 | Buscemi et al. | 623/1 |

FOREIGN PATENT DOCUMENTS

WO 94/21320 9/1994 WIPO.

OTHER PUBLICATIONS

Article entitled "Improved Dilation Catheter Balloons", by Stanley B. Levy, published in the *Journal of Clinical Engineering*, vol. 11, No. 4, Jul.–Aug. 1986.

*Primary Examiner*—Mary Beth Jones
*Attorney, Agent, or Firm*—Vidas, Arrett & Steinkraus

[57] ABSTRACT

The present invention provides an apparatus and method for repairing a diseased vessel at the site of an aneurysm, graft or stenosis. A polymeric self-hardening or self-curing material is introduced into the diseased area. The material is delivered via catheter and allowed to polymerize or cure in situ forming a foam plug in the vessel. A lumen is then created through the foam plug by such means as an atherectomy catheter, to recanalize the vessel. The polymeric material may also be hardened in situ by change in pH or ionic concentration, organic solvents, by permeation of a secondary material capable of precipitation, or by exposure to heat, light or laser energy. In blood, the device may be hardened through a cooperative effect of coagulation, precipitation or ionization. The device can be made of biodegradable material impregnated with growth factors, mitogenic factors or other determinants. The catheter itself may be an ultrasonic imaging catheter.

24 Claims, 1 Drawing Sheet

METHOD AND DEVICE FOR RECANALIZING AND GRAFTING ARTERIES

BACKGROUND OF THE INVENTION

FIELD OF THE INVENTION

The present invention relates generally to treatments for vascular disease and aortic aneurysms and more specifically to a device and method for recanalizing vessels, the device being made of a polymeric material delivered to the site of the defect by a catheter and hardened in situ to form a plug, through which a lumen is formed to recanalize the vessel and form a stent at the site of repair.

SUMMARY OF THE INVENTION

The present invention provides a simple method of repairing vascular disease, aortic aneurysms and the like, either temporarily or permanently, with a biocompatible quick setting polymeric material that hardens in situ in the form of a plug and is subsequently recanalized, leaving behind a stent. The hardenable polymeric material is delivered to the area of defect and recanalized by catheter means.

DETAILED DESCRIPTION TO THE INVENTION

Figure 1:
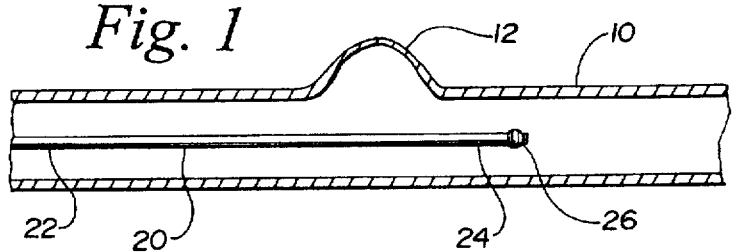
FIG. 1 shows a sectional view of a diseased vessel, showing a typical aneurysm prior to repair according to the present invention. For ease of illustration, the vessel is shown with a catheter according to the present invention inserted therein prior to introduction of the polymeric material.

The present invention is a device for repairing a graft or a diseased vessel at the site of an aneurysm. A polymeric self-polymerizing or curing material is introduced into the diseased area. The material is delivered via catheter and allowed to polymerize or cure in situ forming a plug in the vessel. A lumen is then created through the plug by such means as an atherectomy catheter, to recanalize the vessel.

The present invention also provides an apparatus for recanalizing and grafting a vessel in a body, the apparatus comprising a source of a biocompatible polymeric material in combination with at least one catheter. The biocompatible polymeric material is capable of being delivered in a first state to a repair site in the vessel, and filling the vessel at the repair site in its first state and being further capable of being hardened in situ to a second state to form a plug at the repair site. Delivery means for delivering the biocompatible polymeric material and canalizing means for forming a lumen in said polymeric material after it is hardened may be provided in separate catheters or in one single catheter. The inventive apparatus provides a polymeric vascular graft in a vessel, which is then recanalized.

Preferably the region of the vessel to be repaired is filled with a quick setting material. The most preferred material is a self polymerizing or curing biocompatible foam.

The biocompatible material is delivered via catheter and dilates the vessel, fills the aneurysm and covers grumace and other potential emboli. A lumen is formed by any suitable method such as drilling through the material by an atherectomy catheter or the like to recanalize the artery, i.e. by mechanical means. Alternatively, the biocompatible material may be allowed to harden with the delivery catheter in place, whereby removal of the catheter may recanalize the artery. The remaining material forms a stent or graft structure.

A solid plug may be created in a variety of ways. One possibility is by infusing curable or polymerizable materials. The materials may cure/polymerize because of introduction to the body environment or may do so by the application of energy (e.g. heat or UV light) from a device/catheter. Moisture curable materials would seem to be ideally suited for such an application. Examples of such compounds are cyanoacrylates, polyisocyanate (polyurethane prepolymers), UV curable acrylates, and moisture-curing silicones.

In an alternative embodiment, the plug may be formed by infusion of a solution of a synthetic or biological polymer which precipitates in-vivo. An exemplary infusion would comprise insoluble proteins or polysaccharides in a non-physiologic solution, such as collagen, fibrin or chitosan in acetic acid solution. Another exemplary solution would comprise synthetic polymers in non-aqueous, but water miscible, solvent or solvents, such as dimethyl sulfoxide (DMSO) or latexes which may be pH sensitive.

In a further alternative embodiment, the plug may be formed by infusing a moisture curable cyanoacrylate, butyl cyanoacrylate being the most preferred. In a still further alternative embodiment, fibrin or collagen, especially collagen type IV, dissolved in an appropriate pH aqueous acetic acid solution may be infused. At body pH, the fibrin or collagen will precipitate to form the plug. Additionally, the acidic solution may result in some clot formation which may become incorporated with the precipitated fibrin or collagen, the fibrin or collagen helping to stabilize the clot. A still further alternative embodiment comprises the use of a synthetic polymer, most preferably a biodegradable polymer such as poly-L-lactic acid dissolved in a suitable water miscible solvent, preferably dimethyl sulfoxide.

In addition to polylactic acid, other biodegradable polymers include; polyglycolic acid, polycaprolactone and copolymers of these materials. Additionally, fibrin, collagen and other connective proteins may be copolymerized with these materials.

Within an acceptable period of time, on the order of several seconds to fifteen minutes for example, the plug material will preferably polymerize or cure in place. The plug material may be permeated with biological components such as chemotactic or growth factors, that may be used to alter the reaction of the surrounding tissue. Such components include but are not limited to the group consisting of collagen, fibrin, albumin, βFibroblastic Growth Factor, angiogenic factors, RGD adhesion sequences, antibiotics and mixtures thereof.

The material may be hardened by heat or light energy if it contains crosslinkable moieties. Thus collagen, fibrin, carbohydrates, polylactic or polyglycolic acid or combinations of these could be copolymerized with acrylic acid, or butadiene or other agents containing reactive double bonds. The homopolymer or copolymer may also contain more mobile low molecular weight polymers that could react with the side chains of the main polymer. After expansion into the appropriate shape, energy would be applied to crosslink and thus harden the material. After hardening, a lumen is formed in the plug thereby recanalizing the artery.

The delivery catheter itself, used to introduce the polymeric material, may be an ultrasonic imaging catheter, as is known in the art. The catheter may optionally be controlled from the exterior.

The apparatus and method of the present invention is of particular utility in the treatment of degenerated sections of arteries, which need structural support, such as aneurysms, old vein grafts and the like.

Figure 2:
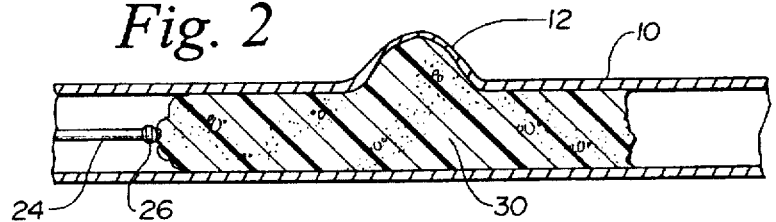
FIG. 2 shows a vessel as in FIG. 1 which has been filled with polymeric material according to the present invention.

Referring now to the figures, FIG. 1 is a sectional view of a diseased vessel 10, showing a typical aneurysm 12 prior to repair according to the present invention. Grumace and stenotic material is apparent. Catheter 20 is inserted and guided to the repair site. Catheter 20 is shown having proximal portion 22 and distal portion, 24. As shown in FIGS. 1 and 2, the biocompatible self polymerizing or self curing polymeric material is provided by a source of polymeric material, indicated at 28. The polymeric material provided by source 28 is delivered by catheter 20, and introduced into the area of repair by foam nozzle 26. It may be necessary to occlude vessel 10 prior to delivery of the polymeric material, which can be accomplished by means well known in the art.

Referring to FIG. 2, vessel 10 is shown after introduction of the polymeric material 30. In the preferred embodiment, polymeric material 30 is a self-hardening polymeric foam. As polymeric material 30 hardens, if forms a plug which fills vessel 10, compresses the grumace and clots present, fills the aneurysm, and may dilate the vessel.

Figure 3:
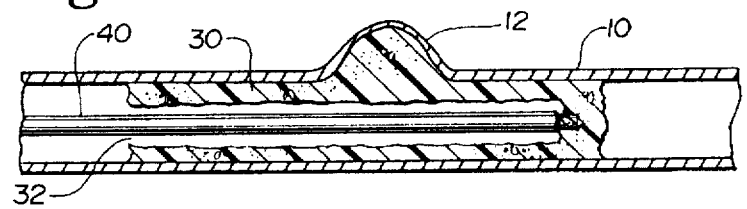
FIG. 3 shows a vessel as in FIG. 2 during recanalization according to the present invention. For ease of illustration, the recanalizing catheter is shown already in place in the hardened polymeric material, in the process of recanalizing the vessel.

Referring to FIG. 3, a lumen 32 is formed in polymeric material 30 by any suitable means. The most preferred means is an atherectomy catheter 40, as shown. The formation of lumen 32 recanalizes the artery. Polymeric material 30 is retained in the repair site as a graft or stent. The atherectomy catheter may include an aspiration lumen to aid in the removal of the material. Additionally, the atherectomy device may be steerable to facilitate the recanalization of any side branches which may have been occluded by the foam.

Figure 4:
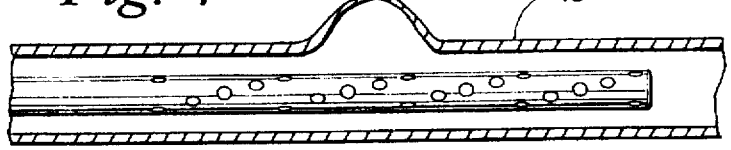
FIG. 4 shows a sectional view of a diseased vessel, showing a typical aneurysm prior to repair according to an alternative embodiment of the present invention. For ease of illustration, the vessel is shown with a catheter according to the present invention inserted therein prior to introduction of the polymeric material.
Figure 5:
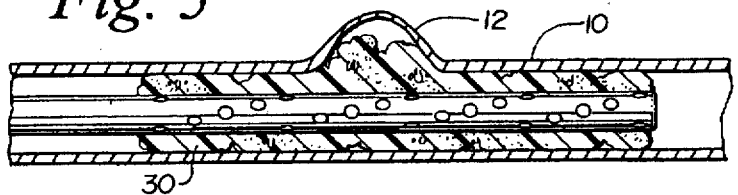
FIG. 5 shows a vessel as in FIG. 4 being filled with polymeric material according to the present invention.
Figure 6:
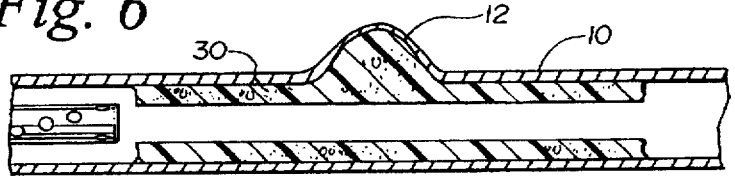
FIG. 6 shows a recanalized vessel with a resulting graft in place, following delivery and hardening of the polymeric material while the delivery catheter is still in place, and subsequent removal of the delivery catheter.

Referring to FIGS. 4–6, an alternative embodiment of the present invention is shown. FIG. 4 shows a sectional view of a diseased vessel 10, showing a typical aneurysm 12 prior to repair according to an alternative embodiment of the present invention. For ease of illustration, vessel 10 is shown with catheter 40 according to the present invention inserted therein prior to introduction of the polymeric material. Catheter 40 has a plurality of recessed delivery holes 42 through which polymeric material 30 is delivered. Catheter 40 also has a non-reactive exterior surface 44. For example, surface 44 may be Teflon® coated. FIG. 5 shows vessel 10 being filled with polymeric material 30 through delivery holes 42 of catheter 40 according to the present invention. Polymeric material 30 is allowed to harden in vessel 10 with catheter 40 in place therein. After polymeric material 30 has hardened, catheter 40 may be removed. The non-reactive surface 44 of catheter 40 releases easily from the polymeric material by twisting catheter 40. Catheter 40 is thereby loosened and removed from polymeric material 30, leaving a channel 46, shown in FIG. 6, therein. FIG. 6 shows vessel 10 following hardening of polymeric material 30 with and removal of delivery catheter 40, leaving a recanalized vessel 10 with the resulting graft in place.

The practice of the present invention achieves several objectives and advantages. The device and method of the present invention provides an advantage over surgery in that the cost of the procedure is substantially less, the risk of infection is less, the hospital residency time is less and there is no physically deforming scar.

In comparison with other methods of providing a stent or graft, the device of the present invention has the advantage of adhering to tissue immediately. It can promote healing at a rapid rate. There is less risk or a recurrence of an aneurysm if the device fills the defect rather than sitting on the surface of the tissue at the site of the defect since the diseased tissue can be quite filamentous. The device of the present invention may be utilized to treat arteries which have no aneurysm, but are stenosed, especially if the expanding foam provides a radial dilation pressure in excess of one or two atmospheres.

The foam delivery catheter may have two delivery lumens, one for a monomer or first chemical and second for a catalyst or second chemical. These could be mixed immediately prior to leaving or immediately after leaving the catheter so that the catheter can be easily removed (i.e., if a single hardenable material is delivered and it sets up in the delivery catheter, the catheter may be difficult to remove).

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A medical device comprising a biocompatible polymeric material which is adapted to be delivered in a first state to a repair site in a vessel, said material being adapted to fill the repair site in its first state and being further adapted to be hardened in situ to form a plug at the repair site, said plug being adapted to have to lumen formed therein in situ, whereby said vessel is recanalized and a polymeric graft is created therein.

2. The device of claim 1 wherein the polymeric material comprises a self polymerizing polymeric foam.

3. The device of claim 1 wherein the polymeric material is adapted to be hardened in situ by chemical means.

4. The device of claim 1 wherein the polymeric material is a moisture curable material selected from the group consisting of cyanoacrylates, polyisocyanates, polyurethane prepolymers, UV curable acrylates, and moisture-curing silicones.

5. The device of claim 4 wherein the polymeric material further includes bioactive components.

6. The device of claim 5 wherein the bioactive components are selected from the group consisting of collagen, fibrin, albumin, βFibroblastic Growth Factor, angiogenic factors, RGD adhesion sequences, antibiotics and mixtures thereof.

7. A medical device comprising a biocompatible polymeric material which is adapted to be delivered in a first state to a repair site in a vessel, said polymeric material comprising an infusion of a solution of a synthetic or biological polymer which precipitates in-vivo, said material being adapted to fill the repair site in its first state and being further adapted to be hardened to form a plug at the repair site, said hardened material being further adapted to have a lumen formed therein, whereby a lumen is formed in said plug, thereby recanalizing file vessel and creating a polymeric graft therein.

8. The device of claim 7 wherein the infusion comprises normally insoluble proteins or polysaccharides in non-physiologic solution.

9. The device of claim 7 wherein the infusion comprises synthetic polymers in a non-aqueous but water miscible solvent.

10. A method for recanalizing and grafting a vessel, the method comprising the steps of:
   a. providing a polymeric material;
   b. delivering the polymeric material to a site needing repair in a vessel by means of a catheter, thereby forming a plug in said vessel; and
   c. canalizing the plug, whereby a stent is formed and the vessel is recanalized.

11. The method of claim 10 wherein the plug is canalized by catheter means.

12. The method of claim 11 wherein the catheter means further comprises an atherectomy means and the plug is canalized by said atheterctomy means.

13. Apparatus for recanalizing and grafting a vessel in a body, the apparatus comprising:
   a. a source of a biocompatible polymeric material, said material being adapted to be delivered in a first state to a repair site in the vessel, and filling the vessel at the repair site in its first state and being further adapted to be hardened in situ to a second state to form a plug at the repair site;
   b. a delivery catheter comprising delivery means located therein for delivering said material in its first state to the repair site in the vessel; and
   c. a second catheter comprising canalizing means located therein for forming a lumen in said material after hardening;
   whereby a polymeric graft is formed and the vessel is recanalized.

14. The apparatus of claim 13 wherein the polymeric material is biodegradable.

15. The apparatus of claim 13 wherein the polymeric material is non-biodegradable.

16. The apparatus of claim 13 wherein the polymeric material includes growth factors and other mitogenic agents.

17. The apparatus of claim 13 wherein the polymeric material is self hardening.

18. The apparatus of claim 13 wherein the polymeric material is adapted to be hardened by chemical means.

19. The apparatus of claim 13 wherein the polymeric material is adapted to be hardened by means of light or heat energy.

20. The apparatus of claim 13 wherein the polymeric material is comprised of a material selected from the group consisting of caprolactone, polylactic acid and mixtures thereof.

21. The apparatus of claim 20 wherein the polymeric material further includes a bioactive material.

22. The apparatus of claim 13 wherein the polymeric material is delivered through an infusion of a solution of a synthetic or biological polymer which precipitates in-vivo.

23. The apparatus of claim 22 wherein the infusion comprises normally insoluble proteins or polysaccharides in non-physiologic solution.

24. The apparatus of claim 22 wherein the infusion comprises synthetic polymers in non-aqueous but water miscible solvent.

* * * * *